United States Patent
Hiyama et al.

(10) Patent No.: US 9,896,408 B2
(45) Date of Patent: Feb. 20, 2018

(54) METHOD FOR PRODUCING AZIDO-AMINE DERIVATIVE

(71) Applicant: FUJIFILM FINECHEMICALS CO., LTD, Hiratsuka-shi, Kanagawa (JP)

(72) Inventors: Tadashi Hiyama, Hiratsuka (JP); Zhiyong Yang, Hiratsuka (JP); Takashi Nagayama, Hiratsuka (JP)

(73) Assignee: FUJIFILM FINECHEMICALS CO., LTD., Hiratsuka-shi, Kanagawa (JP)

( * ) Notice: Subject to any disclaimer, the term of this patent is extended or adjusted under 35 U.S.C. 154(b) by 0 days.

(21) Appl. No.: 15/342,273

(22) Filed: Nov. 3, 2016

(65) Prior Publication Data
US 2017/0121272 A1    May 4, 2017

Related U.S. Application Data

(60) Provisional application No. 62/250,685, filed on Nov. 4, 2015.

(51) Int. Cl.
C07C 209/86    (2006.01)
C07C 209/42    (2006.01)

(52) U.S. Cl.
CPC .......... *C07C 209/42* (2013.01); *C07C 209/86* (2013.01)

(58) Field of Classification Search
CPC .................................................. C07C 209/86
See application file for complete search history.

(56) References Cited

PUBLICATIONS

Communication dated May 3, 2016, from the European Patent Office in counterpart European Application No. 15193140.9.
Frédéric Coutrot et al., "Controlling the Chair Conformation of a Mannopyranose in a Large-Amplitude [2]Rotaxane Molecular Machine", Chemistry a European Journal Supporting Information, Copyright Wiley-VCH Verlag GmbH & Co. KGaA, 69451 Weinheim, 2009, vol. 15, No. 21, Feb. 2009, XP055267864, (49 Pages Total).
Marcel Wieland et al., "Cucurbit[6]uril as a potential catalyst for the acidic decomposition of azidoaminoalkanes", Elsevier, Tetrahedron Letters, vol. 53, No. 33, 2012, (pp. 4351-4353) DOI: 10.1016/J.TETLET.2012.06.016, XP028427769.
Jae Wook Lee et al., "An efficient and practical method for the synthesis of mono-N-protected α,ω-diaminoalkanes", Pergamon, Tetrahedron Letters, vol. 42, 2001, (pp. 2709-2711).
Zhao-Sheng Hou et al., "Synthesis, characterization and properties of side-chain pseudopolyrotaxanes consisting of cucurbituril[6] and poly-$N^1$-(4-vinyl benzyl)-1,4-diaminobutane dihydrochloride", Polymer, vol. 47, 2006, (pp. 742-750).

*Primary Examiner* — Rebecca L Anderson
*Assistant Examiner* — Karen Cheng
(74) *Attorney, Agent, or Firm* — Sughrue Mion, PLLC

(57) ABSTRACT

A method for producing an azido-amine derivative includes obtaining an azido-amine derivative and extracting the azido-amine derivative obtained by using an aromatic solvent or an ether solvent.

1 Claim, 1 Drawing Sheet

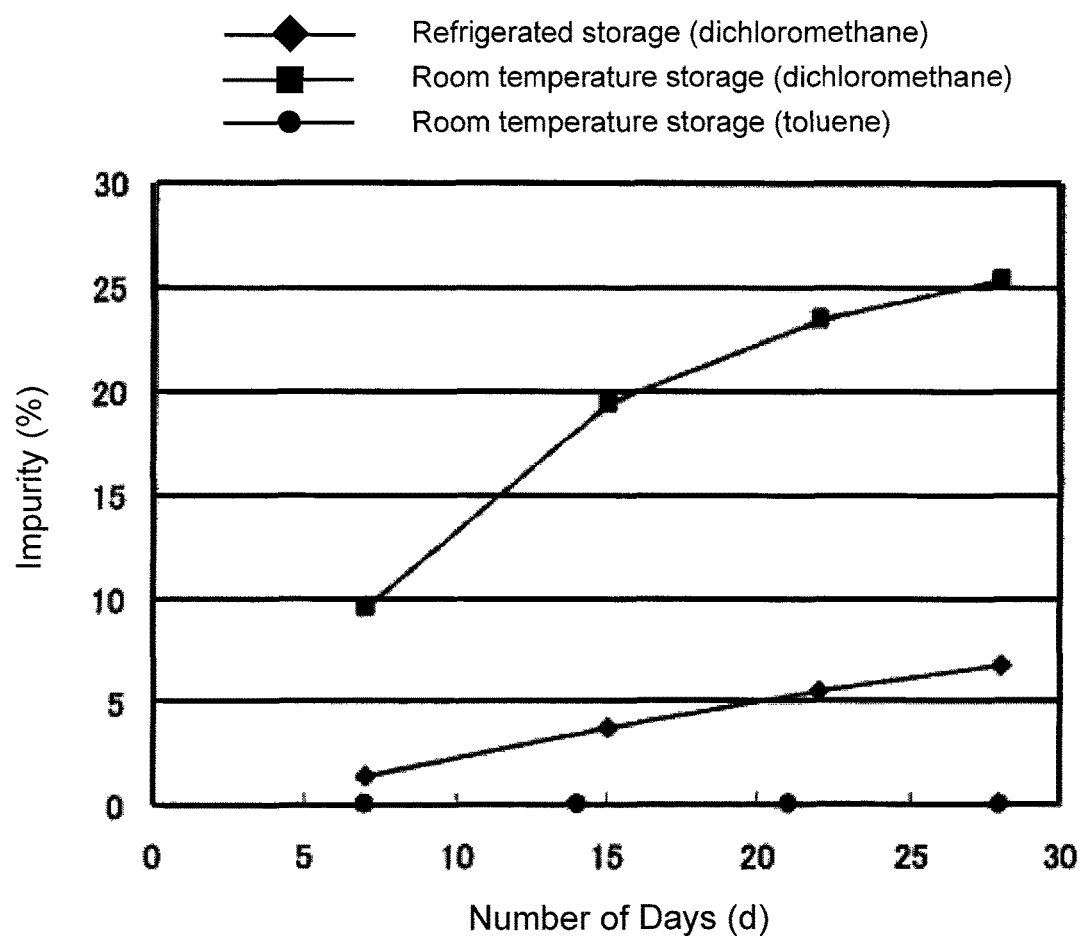

METHOD FOR PRODUCING AZIDO-AMINE DERIVATIVE

CROSS-REFERENCE TO RELATED APPLICATION

This application is based on and claims priority under 35 USC 119 from U.S. Provisional Patent Application No. 62/250,685, filed on Nov. 4, 2015.

BACKGROUND OF THE INVENTION

Technical Field

The present invention relates to a method for producing an azido-amine derivative which is useful as an intermediate of a medicine or the like.

Background Art

The azido-amine derivative is important as an intermediate of a medicine or the like, and various production methods thereof have been hitherto developed. As an example, in the case of 4-azidobutylamine, methods wherein 1,4-dibromobutane as a raw material is diazidated and then subjected to a reduction reaction are known (Tetrahedron Letters, Vol. 42, 2001, pages 2709 to 2711 and Polymer, Vol. 47, 2006, pages 742 to 750). According to these methods, after the completion of the reduction reaction, a hydrochloride of the objective compound is converted to a free form and subjected to liquid separation extraction using methylene chloride as a solvent and then condensation is conducted. However, the use of methylene chloride has problems in that (i) the objective compound undergoes time-lapse degradation, (ii) abnormal heat generation of the solution occurs at the time of condensation and the initiation temperature thereof is low as about 82° C. to cause a problem on safety, and (iii) methylene chloride is carcinogenic and not preferred to the human body.

SUMMARY

An object of the invention is to provide a method for producing an azido-amine derivative which overcomes the problems of time-lapse degradation, safety and the like and is capable of performing the mass production in an industrial scale.

As a result of the intensive investigations to achieve the object described above, the inventors have found that the time-lapse degradation of the objective compound is inhibited and the heat generation initiation temperature at the time of condensation shifts to higher temperature by using an aromatic solvent or an ether solvent at the time of post treatment to complete the invention. Specifically, the invention may be achieved by the following means.

[1] A method for producing an azido-amine derivative, the method including: a step of obtaining an azido-amine derivative represented by formula (II) shown below; and a step of extracting the azido-amine derivative represented by formula (II) shown below, obtained by using an aromatic solvent or an ether solvent:

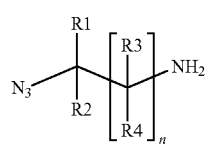

(II)

wherein in the formula, R1 to R4, which may be the same or different, each represent a hydrogen atom, an alkyl group, an aryl group or a heterocyclic residue, and the alkyl group, the aryl group or the heterocyclic residue may further have a substituent, and n represents an integer from 1 to 11, and when n is 2 or more, a plurality of R3 and R4 may be the same or different.

[2] The method for producing an azido-amine derivative according to [1], wherein the aromatic solvent is toluene.

[3] The method for producing an azido-amine derivative according to [1], wherein the ether solvent is diisopropyl ether or tert-butyl methyl ether.

According to a method for producing an azido-amine derivative in an aspect of the invention, an azido-amine derivative which is important as an intermediate of a medicine, a pesticide, a photosensitive material, an electronics material or the like is able to be produced easily in an industrial scale.

BRIEF DESCRIPTION OF THE DRAWING

The FIGURE is a graph showing the results of Example 2 and Comparative Examples 1 and 2.

DETAILED DESCRIPTION OF THE INVENTION

The invention will be described in more detail hereinafter.

The invention relates to a method for producing an azido-amine derivative including obtaining an azido-amine derivative represented by formula (II) shown below and extracting the azido-amine derivative represented by formula (II) shown below thus-obtained using an aromatic solvent or an ether solvent.

A method for obtaining the azido-amine derivative represented by formula (II) shown below is not particularly limited, and known methods can be used. Preferably, a method of reducing a diazide derivative represented by formula (I) shown below to obtain the azido-amine derivative represented by formula (II) shown below is exemplified.

Further, it is preferred to perform condensation after the extracting the azido-amine derivative represented by formula (II) shown below obtained using an aromatic solvent or an ether solvent. A method of condensation is not particularly limited, and known methods can be used. For example, reduced pressure distillation is preferably exemplified.

The diazide derivative represented by formula (I) shown below which can be used as a raw material in the invention is able to prepare by diazidation of a commercially available dihalogenoalkane compound according to a known method (for example, Jikken Kagaku Koza (Forth Edition), Vol. 20, Chapter 8, published by Maruzen Co., Ltd.).

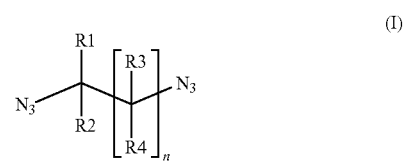

(I)

In the formula, R1 to R4, which may be the same or different, each represent a hydrogen atom, an alkyl group, an aryl group or a heterocyclic residue, and the alkyl group, the aryl group or the heterocyclic residue may further have a substituent.

n represents an integer from 1 to 11. When n is 2 or more, a plurality of R3 and R4 may be the same or different.

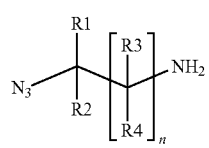
(II)

In the formula, R1 to R4, which may be the same or different, each represent a hydrogen atom, an alkyl group, an aryl group or a heterocyclic residue, and the alkyl group, the aryl group or the heterocyclic residue may further have a substituent.

n represents an integer from 1 to 11. When n is 2 or more, a plurality of R3 and R4 may be the same or different.

In formulas (I) and (II) described above, the alkyl group represented by any one of R1 to R4 may be any of straight-chain, branched and cyclic alkyl groups, and includes, for example, a straight-chain, branched or cyclic alkyl group having from 1 to 12 carbon atoms, for example, methyl, ethyl, propyl, butyl, pentyl, hexyl, heptyl, octyl, nonyl, decyl, undecyl, dodecyl, cyclopentyl, cyclohexyl, cycloheptyl or cyclooctyl.

The aryl group represented by any one of R1 to R4 includes a 6- to 10-membered monocyclic or dicyclic aryl group, for example, phenyl or naphthyl.

The heterocyclic residue represented by any one of R1 to R4 includes a 5- to 10-membered monocyclic or dicyclic heterocyclic residue containing at least one of a nitrogen atom, an oxygen atom and a sulfur atom, for example, imidazolyl, oxazolyl, triazolyl, thiazolyl, 1,3,4-thiadiazolyl, pyridyl, pyrimidyl, pyrazyl, furyl, thienyl, benzothiazolyl, benzoxazolyl or quinolyl.

Each of R1 to R4 is preferably a hydrogen atom, an alkyl group having from 1 to 6 carbon atoms or a phenyl group, more preferably a hydrogen atom or an alkyl group having from 1 to 4 carbon atoms, and particularly preferably a hydrogen atom.

The alkyl group, the aryl group or the heterocyclic residue may further have a substituent. The further substituent is not particularly limited as long as it does not cause a side reaction, and includes, for example, an alkyl group, an aryl group or a heterocyclic residue.

n represents an integer from 1 to 11. n is preferably an integer from 1 to 7, more preferably an integer from 2 to 5, and particularly preferably 3.

The reduction method of diazide derivative can be performed by a known method (for example, Jikken Kagaku Koza (Forth Edition), Vol. 20, Chapter 6, published by Maruzen Co., Ltd.).

Specifically, catalytic reduction using platinum, Raney nickel, palladium-carbon (Pd—C), ruthenium, Lindlar catalyst or the like; and reduction using triphenylphosphine, diborane, sulfide, sodium borohydride or the like are exemplified. The reduction method may be appropriately selected, and a reduction reaction using triphenylphosphine is preferred.

In the case of using triphenylphosphine, the use amount thereof is ordinarily from 0.9 to 3.0 mol, preferably from 1.0 to 2.5 mol, more preferably from 1.1 to 2.0 mol, based on 1 mol of the diazide derivative.

The reduction reaction with triphenylphosphine is preferably performed in a two layer system of an organic solvent and an aqueous acid solution. The organic solvent used is not particularly limited as long as it dissolves a substrate, is water-insoluble and does not disturb the reaction. Specifically, an aliphatic solvent such as pentane, hexane, heptane, octane, nonane, decane, undecane, dodecane, tridecane, 2-methyldodecane, 4-ethylundecane, tetradecane, pentadecane, 3,3-dimethyltridecane, hexadecane, heptadecane and 2-methyl-4-ethyltetradecane; an aromatic solvent such as toluene, xylene, styrene, benzene, phenol, ethylbenzene, diethylbenzene, isopropylbenzene and diphenylmethane; an ether solvent such as diisopropyl ether, tert-butyl methyl ether, diethyl ether and methyl cyclopentyl ether; a glycol solvent, such as ethylene glycol diacetate, ethylene glycol distearate, ethylene glycol diacrylate, diethylene glycol diacetate and diethylene glycol diacrylate; and a hydrogenated aromatic solvent, such as 1,4-dihydronaphthalene, 1,2,3,4-tetrahydronaphthalene, 9,10-dihydroanthracene, 9,10-dihydrophenanthrene, 4,5,9,10-tetrahydropyrene, 1,2,3,6,7,8-hexahydropyrene and dodecahydrotriphenylene.

Of the solvents, the aromatic solvent and the ether solvent are preferred, and toluene, diisopropyl ether, tert-butyl methyl ether are more preferred.

The amount of the solvent used may vary according to the substrate, and is ordinarily from 4 to 10 ml, preferably from 5 to 8 ml, based on 1 g of the diazide derivative.

The acid which is used as the aqueous solution is not particularly limited as long as it is able to form an addition salt, and is preferably an inorganic acid, such as hydrochloric acid, sulfuric acid and phosphoric acid, and more preferably hydrochloric acid or sulfuric acid.

The amount of the acid used is ordinarily from 0.9 to 2.7 molar equivalent, preferably from 1.0 to 2.5 molar equivalent, and more preferably from 1.2 to 2.0 molar equivalent.

In the reaction, an appropriate amount of water is added to the system in addition to the acid described above. The amount of water added is from 0.1 to 1.5 ml, preferably from 0.2 to 1.2 ml, more preferably from 0.3 to 1.0 ml, based on 1 ml of the organic solvent used.

The reaction temperature is ordinarily in a range from 0 to 20° C., and preferably from 5 to 10° C. The reaction is ordinarily terminated within 24 hours, and disappearance of the raw materials is recognized from 8 to 20 hours in many cases.

After the completion of the reduction reaction, the objective compound obtained is subjected to liquid separation extraction and then condensation of post treatment is preferably conducted. The solvent used in the step is the aromatic solvent or the ether solvent described above.

As the aromatic solvent, toluene, xylene, styrene, benzene, phenol, ethylbenzene, diethylbenzene, isopropylbenzene, diphenylmethane and the like are exemplified, and toluene is particularly preferred.

As the ether solvent, diisopropyl ether, tert-butyl methyl ether, diethyl ether, methyl cyclopentyl ether and the like are exemplified, and diisopropyl ether and tert-butyl methyl ether are particularly preferred.

The solvent used at the reduction reaction and the solvent for the post treatment may be the same or different from each other, and it is preferred to use the same solvent from the standpoint of operability and cost.

The number of times of the liquid separation is ordinarily from 2 to 7, and preferably from 2 to 5. The amount of the solvent used in one time of the liquid separation is from 1 to 10 ml, preferably from 2 to 5 ml, based on 1 g of the azido-amine derivative.

The organic layers obtained by the liquid separation extraction are preferably brought together and subjected to condensation under a reduced pressure. The degree of the reduced pressure at the condensation is ordinarily from 1.0 to 20 pKa, and preferably from 3.0 to 7.0 pKa. The temperature at the condensation is ordinarily from 0 to 60° C., and preferably from 5 to 40° C.

EXAMPLES

The invention will be described specifically with reference to the examples, but the invention should not be construed as being limited thereto.

The reaction tracking and yield of the objective compound were performed by $H^1$-NMR (measurement solvent: DMSO), and as to the presence or absence of the impurity, the content thereof was analyzed from a ratio of peak areas obtained by using high performance liquid chromatography (HPLC).

The measurement conditions of HPLC were as follows. Column: ODS-80TS; Eluent: methanol/water (v/v=7/3); Buffer solution: 0.1% acetic acid; Detector: RI; Flow rate: 1.0 ml/min; Column temperature: 40° C.

Example 1: Synthesis of 4-Azidobutylamine 150.0 g (694.7 mmol) of 1,4-dibromobutane was dissolved into 150 ml of dimethylformamide, and an aqueous solution prepared by dissolving 150.0 g (2.31 mol) of sodium azide in 450 ml of water was added dropwise thereto, and the mixture was stirred at an internal temperature from 80 to 85° C. for 8 hours. After the completion of the reaction, the internal temperature was cooled to 30° C., 375 ml of water and 300 ml of toluene were added thereto, the mixture was stirred for 5 minutes, and then subjected to liquid separation. The aqueous layer was extracted again with 300 ml of toluene, and two toluene layers obtained were brought together and washed with 343.7 g of a 20% aqueous sodium chloride solution to obtain a toluene solution of 1,4-diazidobutane.

Subsequently, the total volume of the toluene solution of 1,4-diazidobutane was cooled to an internal temperature from 5 to 10° C., 107.0 g (1.03 mol) of commercially available hydrochloric acid and 418 ml of water were added thereto, then 199.5 g (76.1 mmol) of triphenylphosphine and 750 ml of toluene were added thereto under nitrogen atmosphere, followed by performing reaction (reduction reaction) under the nitrogen atmosphere for 12 hours. The reaction solution was filtered and then subjected to liquid separation, and the aqueous layer obtained was washed twice with 300 ml of toluene. Then, the aqueous layer was cooled to an internal temperature from 0 to 5° C., an aqueous solution prepared by dissolving 150.0 g (266.6 mmol) of sodium hydroxide in 225 ml of water was added dropwise thereto, and the mixture was stirred for 20 minutes. Extraction and liquid separation were performed by adding 450 ml of toluene, and the organic layer obtained was subjected to condensation under a reduced pressure of 6.7 kPa or more and at an internal temperature of 35° C. or less to obtain 65.8 g of the oily objective compound. The conversion yield by NMR was 83%.

Example 2

The oily objective compound (reduced pressure condensate) obtained in Example 1 was stored at room temperature and a generation rate of impurity was measured.

Comparative Examples 1 and 2: Synthesis of 4-Azidobutylamine 4-azidobutylamine was synthesized in the same manner as in Example 1 except that the reaction solvent of the reduction reaction and the extraction solvent after the reduction reaction were changed from toluene to dichloromethane, and storage at room temperature (Comparative Example 1) and refrigerated storage at 5° C. or less (Comparative Example 2) were conducted, and the generation rate of impurity was measured in the same manner as in Example 1.

The results of Example 2 and Comparative Examples 1 and 2 are shown in FIG. 1.

It is apparent from the results shown in FIG. 1 that in the case of using toluene, the impurity is hardly generated even after the room temperature storage for 4 weeks and toluene has an effect on inhibiting the time-lapse degradation.

Example 3

Synthesis was performed in the same manner as in Example 1 except that the reaction solvent of the reduction reaction and the extraction solvent after the reduction reaction were changed from toluene to tert-butyl methyl ether (abbreviated as MTBE).

Examples 4 to 7 and Comparative Examples 3 and 4

Using the objective compounds obtained in Examples 1 and 3 and Comparative Example 1, the solutions having the concentration shown in Table 1 were prepared, and heat generation amount and heat generation temperature were measured by a differential scanning calorimeter (DSC).

The measurement conditions of DSC were as follows. Equipment: DSC 6200 produced by SII Nano Technology Inc.; Temperature program: from 30 to 400° C.; Container: plated with Au The results obtained are shown in Table 1.

TABLE 1

| | Solvent Used | Content (%) | Heat Generation Amount (mJ/mg) | Heat Generation Initiation Temperature (° C.) | Heat Generation Peak Temperature (° C.) |
|---|---|---|---|---|---|
| Example 4 | Toluene | 62 | 1449 | 145.8 | 239 |
| Example 5 | Toluene | 84 | 1649 | 152.5 | 233.9 |
| Example 6 | MTBE | 60 | 1267 | 147.6 | 233.0 |
| Example 7 | MTBE | 84 | 1497 | 140.0 | 228.7 |
| Comparative Example 3 | Dichloromethane | 60 | 2076 | 81.7 | 247.1 |
| Comparative Example 4 | Dichloromethane | 86 | 1579 | 124.1 | 229.3 |

MTBE denotes tert-butyl methyl ether.

In the case of ordinary compounds, as the concentration of the solution thereof is higher, dangerousness such as explosiveness or heat generation increases. However, in the case of azido-amine derivative according to the invention, as to the dichloromethane solution thereof, as the concentration of the solution thereof is lower, the heat generation initiates at lower temperature. It is considered that this is because the excess amount of dichloromethane before the initiation of condensation reacts with the azido-amine derivative to generate impurities.

Since the heat generation initiation temperature decreases and the heat generation amount increases in the state of low concentration, considerably dangerous conditions occur in the way of condensation. From this fact it is clear that the method according to the invention is able to avoid danger.

The invention relates to a method for producing azido-amine which exerts the effect on inhibiting the time-lapse degradation and has high safety, and is an extremely practical production method which is able to synthesize the objective compound without problems even in the industrial scale.

What is claimed is:

1. A method for producing an azido-amine derivative of formula (II), the method comprising:
   a step of obtaining an azido-amine derivative represented by formula (II) shown below; and
   a step of extracting the azido-amine derivative represented by formula (II) shown below, obtained by using toluene as an aromatic solvent:

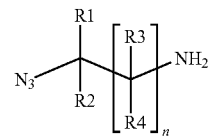
(II)

wherein in the formula, R1 to R4, which may be the same or different, each represent a hydrogen atom, an alkyl group, an aryl group or a heterocyclic residue, and the alkyl group, the aryl group or the heterocyclic residue may further have a substituent, and n represents an integer from 1 to 11, and when n is 2 or more, a plurality of R3 and R4 may be the same or different.

* * * * *